United States Patent [19]

Forrest et al.

[11] Patent Number: 5,077,197
[45] Date of Patent: Dec. 31, 1991

[54] USE OF CHARGE TRANSFER COMPLEXES IN ASSAY

[75] Inventors: Gordon C. Forrest, East Horsley; Simon J. Rattle, Quainton; Grenville A. Robinson, London, all of United Kingdom

[73] Assignee: Serono Diagnostics Limited, England

[21] Appl. No.: 707,661

[22] Filed: Mar. 4, 1985

[30] Foreign Application Priority Data

Mar. 5, 1984 [GB] United Kingdom ............... 8405691

[51] Int. Cl.$^5$ ............... G01N 33/53; G01N 33/543; G01N 33/536; G01N 33/531
[52] U.S. Cl. ............... 435/7.1; 435/975; 436/501; 436/518; 436/536; 436/537; 436/538; 436/543; 436/547; 436/805; 436/806; 436/808; 436/904
[58] Field of Search ............... 436/536, 537, 538, 541, 436/805, 806, 501, 518, 543, 547, 149, 808; 435/7.1, 975

[56] References Cited

U.S. PATENT DOCUMENTS

| | | | |
|---|---|---|---|
| 4,233,144 | 11/1980 | Pace et al. | 436/806 |
| 4,279,993 | 7/1981 | Magers et al. | 436/805 |
| 4,280,815 | 7/1981 | Oberhardt et al. | 436/805 |
| 4,287,300 | 9/1981 | Gibbons et al. | 436/805 |
| 4,385,114 | 5/1983 | Guthlein et al. | 436/810 |
| 4,444,892 | 4/1984 | Malmros | 436/528 |

FOREIGN PATENT DOCUMENTS 0078636  5/1983  European Pat. Off. .

OTHER PUBLICATIONS

Sharp, et al., J. Electroanal. Chem., vol. 109 (1980), pp. 271–288.

*Primary Examiner*—Esther L. Kepplinger
*Assistant Examiner*—Florina B. Hoffer
*Attorney, Agent, or Firm*—Ostrolenk, Faber, Gerb & Soffen

[57] ABSTRACT

A method of assaying a ligand in a sample which method includes the steps of contacting the sample with components comprising
(a) a specific binding partner to the ligand and, if desired,
(b) at least one reagent selected from ligand analogues and specific binding, partners,
at least one of the said components (a) and (b) being labelled with an electron-donor or electron-acceptor, and determining whether (and, if desired, the extent to which) transfer of electrons between the said electron-donor or electron-acceptor label and a suitable charge-transfer partner resulting in charge-transfer complex formation is perturbed by ligand complex formation and/or by controlled external influences.

14 Claims, No Drawings

USE OF CHARGE TRANSFER COMPLEXES IN ASSAY

The present invention relates to methods of assay of one of a pair of specific binding partners, and to kits of reagents for carrying out these methods.

There is today a great need for rapid and accurate methods of assaying biologically active substances (which may be at low concentration), particularly in body fluids such as blood, saliva or urine. A wide variety of medical conditions, such as pregnancy, drug overdose, metabolic birth defects, hormonal disorders and diabetes can be diagnosed using such assay techniques.

Many assay methods rely on the formation of a complex between the species under assay (hereinafter called "ligand") and another species to which it will bind specifically (hereinafter called "specific binding partner"). The extend of complex formation is a function of the amount of the ligand present.

The assay of ligand is determined by monitoring the extent of complex formation, for example by the use of chemical or biochemical labels. Several methods of labelling have been employed, for example radioisotopic or enzyme labelling, spin-labelling or labelling employing fluorescent or bioluminescent species.

The use of radioisotopic labels has been particularly widespread, due to the high degree of sensitivity and specificity obtainable. There are, however, serious disadvantages to the use of radioactive labels. Radioactive labels have limited shelf life due to spontaneous decay, necessitating frequent recalibration of the equipment, and their use will require adherence to strict safety precautions and is subject to legal regulation. These disadvantages will inevitably lead to higher costs and the necessity for high standards of sophistication of equipment, laboratory facilities and personnel.

An alternative to radioisotopic labels which has been employed is an enzyme label, in which the label is monitored indirectly (for example by measuring the removal of enzyme substrate or the generation of the product of the enzyme-catalysed reaction by spectrophotometry optionally using a secondary reaction involving a chromogen, by nephelometry, by fluorimetry or by radiometry). Such monitoring techniques may lack the high degree of sensitivity and specificity required for modern assay work. This may be due to the fact that neither the primary nor the secondary reaction is 100% quantitative or there may be inaccuracy in end-point assessment. The use of radiometry presents the usual problems of safety and short shelf-life of the reagents. The chromogens used in spectrophotometric techniques are often carcinogenic.

Furthermore, a separation step may be necessary following the formation of the labelled complex in order to remove unbound labelled component from the system before determination of the amount of labelled complex by the usual counting methods.

The present invention has as one of its objects the provision of a sensitive and specific method of ligand assay, avoiding the use of radioactive species or enzyme labels.

Thus, in its broadest aspect, the invention provides a method of assaying a ligand in a sample which method includes the steps of contacting the sample with components comprising (a) a specific binding partner to the ligand and, if desired,
(b) at least one reagent selected from ligand analogues (as herein defined) and specific binding partners, at least one of the said components (a) and (b) being labelled with an electron-donor or electron-acceptor, and determining whether (and, if desired, the extent to which) transfer of electrons between the said electron-donor or electron-acceptor label and a suitable charge-transfer partner resulting in charge-transfer complex formation is perturbed by ligand complex formation and/or by controlled external influences.

The method of the present invention can be used for either qualitative or quantitative assays, the assay being completed by comparing the determined perturbation with calibration data.

The term "ligand analogue" used herein refers to a species capable of complexing with the same specific binding partner as the ligand under assay, and includes inter alia within its scope a known quantity of the ligand under assay.

It will be appreciated that two types of complex will be formed in the assays of the present invention—a complex between the ligand in the sample (and, if present, ligand analogues) and specific binding partners (herein called "ligand complex"), and the charge-transfer complex between the label and a suitable partner (herein called "charge-transfer complex").

When the label used is an electron-donor, the charge-transfer partner will be an electron-acceptor; when the label used is an electron-acceptor, the charge-transfer partner will be an electron-donor.

The formation of the charge-transfer complex results from a transfer of electrons from the donor to the acceptor. This transfer of electrons is perturbed by the formation of the ligand complex, the perturbation being due typically to an inhibition of the transfer of electrons between the charge-transfer partners. The extent of inhibition is a function of the proximity of the site of ligand complex formation to the site of attachment of the label.

The transfer of electrons between the label and its partner on formation of the charge-transfer complex may for example be measured electrically by monitoring a change in the electrical properties (e.g. conductivity, resistivity, capacitance) of the partner on complex formation, or may for example be measured spectrophotometrically by virtue of a change in the colour (or the intensity of colour) which may occur in solution on complex formation.

According to one embodiment of the invention, an electrical method of measurement is used. In this embodiment one partner in the charge-transfer complex will conveniently comprise a solid surface connected to an electrical measuring device (e.g. a sensitive currentmeter). If the label used is an electron-donor, the solid surface will be an electron-acceptor; if the label used is an electron-acceptor, the solid surface will be an electron-donor. The transfer of electrons between the label and its charge-transfer partner may be determined from the change in the electrical properties of the donor or acceptor comprising the solid surface.

In a typical case, formation of the ligand complex perturbs formation of charge-transfer complex at the solid surface. The degree of perturbation can be related to the amount of ligand present in the sample, from calibration data obtained with similar systems using known amounts of ligand.

In one method of the invention, the rate of perturbation of the electrical properties as a result of ligand complex formation may be determined. Conveniently, the initial rate of perturbation will be measured. Such a method is applicable to a competitive assay in which the ligand and a labelled ligand analogue compete for complexing with the specific binding partner. The reaction may be viewed as competitive inhibition of the ligand complexing reaction by the ligand analogue. Thus, the initial rate of perturbation is related to the concentration of ligand present and from a calibration plot of the initial rate of perturbation v. concentration of ligand present, the ligand assay can be readily determined.

The method of assay involving a determination of the rate of perturbation is also applicable to non-competitive assays where the labelled ligand analogue is absent and sufficient labelled specific binding partner is employed to enable all the ligand introduced to be complexed within the concentration range of interest.

The method of assay involving determination of the chosen electrical property of the solid surface is applicable to the types of assay previously discussed.

The technique involving an electrical measurement is preferably carried out in an apparatus containing an aqueous assay medium comprising inter alia, pH buffer, preferably at constant ionic strength. The components may be added through an entry port provided in the apparatus. Means may be provided for incubating the assay medium at any desired temperature.

The solid surface will typically comprise a pair of electrodes (fabricated from for example, gold, platinum or aluminium deposited on an insulating substrate (for example, alumina, silicon or glass)) over which a thin layer of electron donor or electron acceptor has been deposited. Conventional deposition techniques may be used, for example, vacuum evaporation or solvent casting. Electrical contact made to the electrodes enables the electrical properties of the electron donor or electron acceptor to be monitored. The conditions at the solid surface should be carefully controlled to ensure compatability between the label and the solid surface. Thus an electron-acceptor surface may comprise, for example, tetranitrofluorenone deposited by vacuum evaporation onto a gold electrode.

In an alternative embodiment, a spectrophotometric method of measurement is used. In this embodiment, the partner in the charge-transfer complex will conveniently comprise a chemical species in solution which forms a coloured charge-transfer complex with the label. The extent of formation of such a complex is related to the amount of ligand present and is detectable qualitatively or quantitatively in a spectrophotometer as a change at a specific wavelength or in the intensity of the colour (absorbance) due to formation of the ligand complex.

The spectrophotometric measurement technique is applicable to methods in which an absolute perturbation is measured as an end-point, or in which a rate of perturbation is measured.

The reaction may be performed in any suitable vessel with the sample optionally being transferred to an appropriate cell prior to colour (absorbance) measurement in a spectrophotometer. The aqueous assay medium will typically comprise the appropriate reagents including inter alia, pH buffer. It may be necessary carefully to control the temperature of the assay medium.

In a typical case, formation of the ligand complex perturbs a peak absorbance of light at a predetermined fixed wavelength, the perturbation or rate of perturbation being related to the concentration of ligand in the sample.

In both the electrical and the spectrophotometric techniques, the assay may be a competitive assay in which the sample and labelled ligand analogue are added together to a solution of a specific binding partner reagent and formation of the charge-transfer complex is initiated either immediately or after completion of the ligand complexing reaction and the formation of charge-transfer complex is determined either by rate or absolute measurements.

Alternatively, non-competitive assays may be carried out. So long as there is sufficient labelled specific binding partner present, the absolute perturbation, or the rate of perturbation, in the electrical or spectrophotometric measurements from the initial reading before introduction of the final component, will be dependent on the amount of added ligand and the assay can therefore be calculated with reference to calibration data.

It is preferable that the sample and reagents (a) and, if present, (b) are added in such an order that a ligand complex is formed after introduction of the final component but not prior thereto and that the charge-transfer partner for the label is not added until it is desired to take electrical or spectrophotometric measurements. It is, however, also possible for there to be ligand complex present before the final component is added, in which case the final component will become complexed by displacing one component of the complex. Furthermore, in cases where the charge-transfer complex reaction is reversible, it is possible to prepare the charge-transfer complex before addition of the sample and other reagents and then to take electrical or spectrophotometric measurements.

It may be desirable to incubate the assay medium between the introductions of different reagents to allow the various complexing reactions to proceed. Thus, for example, it may in some cases be necessary for the ligand complexing reaction to reach equilibrium before the charge-transfer complexing reaction is initiated.

It may be found, on measuring the perturbation of an electrical or spectrophotometric characteristic, that no, or only a slight, perturbation is observed due to ligand complex formation. In that case, it may prove advantageous artificially to generate or enhance a perturbation by controlled external influences. Although the magnitude of the external influence may have some bearing on the change induced, and must therefore be consistent with any such influence employed in calibration experiments, it is thought that any change produced in the perturbation remains a function of the ligand complex.

In the electrical technique, the artificial generation or enhancement of the perturbation is preferably performed by displacement of the ligand complex relative to the solid surface (partner for the label), for example by further complexing the ligand complex with a species which will bind specifically thereto, coupled in a conventional way to a solid support (e.g. in the form of magnetisable particles or beads), with subsequent displacement of the support and coupled molecules. In extreme cases, the displacement may constitute complete removal of the complex from the apparatus, but in general the complex will be displaced within the apparatus.

In the spectrophotometric technique, the artificial generation or enhancement of the perturbation is preferably performed by displacement of the ligand complex relative to the unbound ligand, for example by further complexing the ligand complex with a species which will bind specifically thereto, coupled in a conventional way to a solid support, with subsequent displacement of the support and coupled molecules, the spectrophotometic assay being performed on the residual solution. If necessary, the two binding partner-ligand complex formations may be performed in reverse sequence.

The methods of the invention are generally simpler than known methods, in that they may eliminate the need for the separation of complexed and uncomplexed phases before the assaying step.

In a further aspect, the present invention provides kits of reagents and apparatus for carrying out the assays of the invention. When electrical measurements are desired, suitable kits may comprise a solid surface capable of being connected to a sensitive current meter, and an aqueous assay medium with suitable components present (in solution). When spectrophotometric measurements are desired, suitable kits may comprise a spectrophotometric cell containing an aqueous assay medium with suitable components present. In both cases, other components (e.g. further reagents etc) and the sample to be assayed may conveniently be introduced through an entry port provided in the apparatus or cell. The kits may be automated so that the components are added in a predetermined sequence, and the incubation temperature may be controlled automatically.

Advantageously, the kits may be pre-calibrated and provided with a scale whereby the perturbation in the measured characteristic of the components may be read off directly as an amount of ligand in the sample.

The invention will be particularly described hereinafter with reference to an antibody or an antigen as the ligand. However the invention is not to be taken as being limited to assays of antibodies or antigens. Examples of ligands which may be assayed by the method of the invention are given in Table I below, together with an indication of a suitable specific binding partner in each instance.

TABLE I

| Ligand | Specific Binding Partner |
|---|---|
| antigen | specific antibody |
| antibody | antigen |
| hormone | hormone receptor |
| hormone receptor | hormone |
| polynucleotide strand | complementary polynucleotide strand |
| protein A | immunoglobulin |
| immunoglobulin | protein A |
| enzyme | enzyme cofactor (substrate) |
| enzyme cofactor (substrate) | enzyme |
| lectins | specific carbohydrate |
| specific carbohydrate of lectins | lectins |

The methods of the invention have very broad applicability, but of particular interest are the assay of: Hormones, including peptide hormones (e.g. thyroid stimulating hormone (TSH), lutenising hormone (LH), follicle stimulating hormone (FSH) human chorionic gonadotrophin (HCG), insulin or prolactin) and non-peptide hormones (such as thyroxine or tri-iodothyronine), proteins including carcinoembryonic antigen (CEA) and alphafetoprotein (AFP), drugs (e.g. digoxin), sugars, toxins and vitamins.

The method of the invention may be used in particular to assay antigens or antibodies.

The term "antigen" as used herein will be understood to include both permanently antigenic species (for example, proteins, bacteria, bacteria fragments, cells, cell fragments and viruses) and haptens which may be rendered antigenic under suitable conditions (including narcotics, hypnotics, analgesics, cardiovascular drugs, vitamins, hormones, antibiotics, pesticides and sugars).

As mentioned above, the degree of inhibition of the transfer of electrons between electron-donor and electron-acceptor will be a function of the proximity of the site of the ligand complex formation to the site of attachment of the label. Since in general, haptens will be smaller than permanently antigenic species, the methods of the invention may be particularly applicable to assays of permanently antigenic species and antibodies using as labelled reagents, respectively, antibodies and haptens.

It will be understood that the term "antibody" used herein includes within its scope a) any of the various sub-classes of immunoglobulin, e.g. IgG, IgM, derived from any of the animals conventionally used, e.g. sheep, rabbits, goats or mice,
b) monoclonal antibodies,
c) intact molecules or "fragments" of antibodies, monoclonal or polyclonal, the fragments being those which contain the binding region of the antibody, i.e. fragments devoid of the Fc portion (e.g., Fab, Fab', F(ab')$_2$) or the so-called "half-molecule" fragments obtained by reductive cleavage of the disulphide bonds connecting the heavy chain components in the intact antibody.

The method of preparation of fragments of antibodies is well known in the art and will not be described herein.

Labelling of an antibody reagent may be achieved by conventional methods, e.g. using covalent or non-covalent attachment, for example by any of the following methods:

(i) providing the electron-donor or electron-acceptor label with one or more functional groups capable of bonding interactions with the molecular structure of the antibody such that the electron-doning or accepting properties of the label are substantially unimpaired;
(ii) using cross-linking groups;
(iii) using an avidin-biotin binding system (i.e. avidin-carrying antibody binding with biotin-carrying molecules of the desired label, or biotin-carrying antibody binding with avidin-carrying label) to give a system with up to four labels per reagent molecule.

Similar methods may be applied as desired for the labelling of antigen reagents. Suitable methods are known in the art and will not be discussed in detail here.

The particular method of labelling used may be chosen to suit the circumstances of the assay, e.g. the reagent used, the label used, etc. It will generally be desirable to incorporate as many molecules of label as possible into each reagent.

The attachment of the label to the antibody or antigen can generally be via any portion of the two species, so long as the electron-donating or accepting properties of the label and immunological activity of the antibody or antigen are substantially retained.

Suitable labels which may be employed in the techniques of the invention are given in Table II, together with an indication of a suitable partner in the charge-transfer complex. In general, however, any partner which is capable of forming a charge-transfer complex may be employed.

TABLE II

| | Partner | |
|---|---|---|
| Label | Electrical technique | Spectrophotometric technique |
| (Electron-Donors) | | |
| 1,3,5-trimethylbenzene | 1,3,5-trinitrobenzene (solid surface) | 1,3,5-trinitrobenzene |
| Bis-π-benzene chromium | tetracyanoethylene (solid surface) | tetracyanoethylene |
| nitrobenzene | tetrathiofulvalene (solid surface) | tetrathiofulvalene |
| nitrobenzene | tetranitrofluorenone (solid surface) | tetranitrofluorenone |
| nitrobenzene | tetramethylphenanthroline (solid surface) | tetramethylphenanthroline |
| (Electron-Acceptors) | | |
| 1,3,5-trinitrobenzene | 1,3,5-trimethylbenzene (solid surface) | 1,3,5-trimethylbenzene |
| tetracyanoethylene | bis-π-benzene chromium (solid surface) | bis-π-benzene chromium |
| tetrathiofulvalene | nitrobenzene (solid surface) | nitrobenzene |
| tetranitrofluorenone | nitrobenzene (solid surface) | nitrobenzene |
| tetramethylphenanthroline | nitrobenzene (solid surface) | nitrobenzene |

Functionalisation may be required in order to permit successful binding to the antibody or antigen.

Thus, it may be necessary to modify the label molecule by providing one or more side chains, [e.g. side chains of the formula —(CH$_2$)$_n$COOH or —(CH$_2$)$_m$NH$_2$ (where n and m may be e.g. from 0 to 6)] on, for example, benzene rings in the molecule. Additional functional groups may be incorporated into the side chain, typically those groups used in the chemical modification of proteins, for example mercuric chloride, precursors of nitrenes and carbenes, diazo or iodide groups. The terminal —COOH or —NH$_2$ groups are then available to interact with suitable sites in the antibody or antigen molecule.

The length of the side chain (i.e. the value of n or m) will depend primarily on the structure of the antibody or antigen to which the label is to be bound.

The labelled antibody or antigen reagent may be purified prior to use, by methods which are known in the art. Suitable methods include, for example, dialysis, gel filtration, thin layer chromatography, high performance liquid chromatograph and ion-exchange chromatography.

Thus, for example, antigens or antibodies can be assayed by competitive or direct methods according to the invention. All conventional immunoassay techniques which have hitherto been applied with other types of label are applicable analogously to the methods of this invention, including e.g. competitive, displacement and direct techniques.

Where it is desired artificially to generate or enhance a perturbation by displacement of a ligand complex by further complexing with an immobilised species which will bind specifically thereto, the said species may, for example, bind specifically to the ligand if a labelled antibody is employed as a component, or may bind specifically to the specific binding partner of the ligand if a labelled antigen is employed as a component. The two immuno-complexing reactions may be performed in any order, as desired.

By way of example only, the invention includes inter alia the following embodiments:

D = electron-donor
A = electron-acceptor

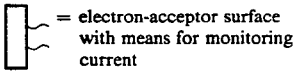 = electron-acceptor surface with means for monitoring current

——< = antibody

◇ = antigen

---> indicates the formation of a charge-transfer complex

—> indicates the formation of a charge-transfer complex

1) Direct assay for the determination of antigen concentration in a sample using labelled antibody Addition of electron-donor-labelled antibody reagent to the sample, followed by introduction of an electron-acceptor surface gives a system where the concentration of (or rate of formation of) charge-transfer complex is inversely related to the antigen concentration:

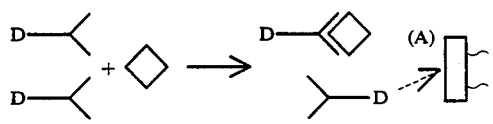

Alternatively, the electron-acceptor may be a reagent in solution and a determination of colour change made:

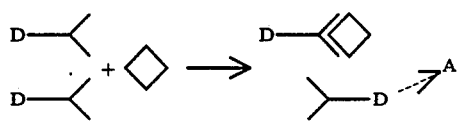

Alternatively, the antibody may be labelled with electron-acceptor and the donor provided as a surface for electrical measurements, or a separate reagent for colorimetric measurements.

2) Direct assay for the determination of antibody concentration in a sample using labelled antigen Addition of electron-donor-labelled antigen reagent to the sample, followed by introduction of an electron-acceptor surface gives a system where the concentration of (or rate of formation of) charge-transfer complex is inversely related to the antibody concentration:

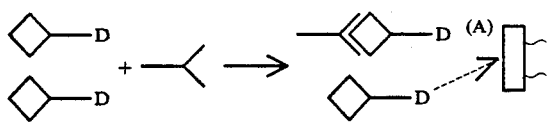

Alternatively, the electron-acceptor may be a reagent in solution and determination of colour change made:

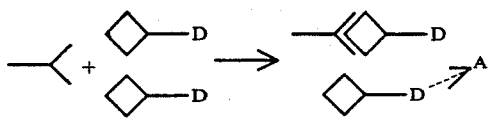

Alternatively, the antigen may be labelled with the electron-acceptor and the donor provided as a surface for electrical measurements, or as a separate reagent for colorimetric measurements.

3) Competitive assay for the determination of antibody concentration in a sample using labelled antibody Addition of electron-donor-labelled antibody to the sample followed by a solution of antigen as a reagent (limited concentration), then an electron-acceptor surface, gives a system where the concentration of (or rate of formation of) charge-transfer complex is directly related to the concentration of antibody in the sample:

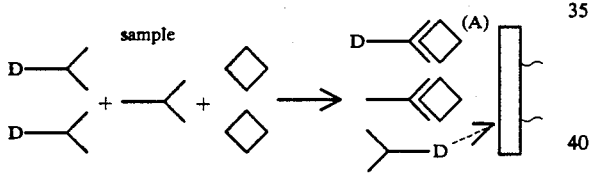

Alternatively, the electron-acceptor could be a reagent in solution and a determination of colour change made:

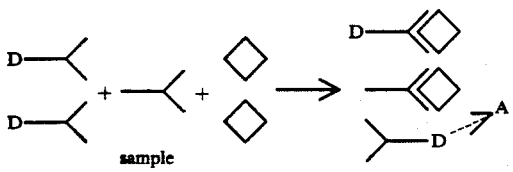

Alternatively, the antibody may be labelled with the electron-acceptor and the donor provided as a surface for electrical measurements or as a separate reagent for colorimetric measurements.

4) Competitive assay for the determination of antigen concentration in a sample using labelled antigen Addition of electron-donor-labelled antigen to the sample followed by a solution of antibody as a reagent (limited concentration), then an electron-acceptor surface, gives a system where the concentration of (or rate of formation of) charge-transfer complex is directly related to the concentration of antigen in the sample:

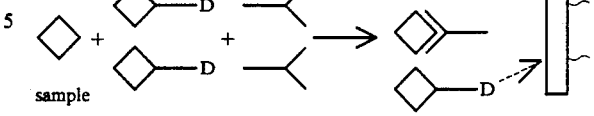

Alternatively, the electron-acceptor may be a reagent in solution and determination of colour change made:

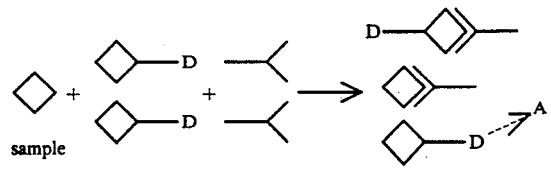

Alternatively, the antigen may be labelled with the electron-acceptor and the donor provided as a surface for electrical measurements or as a separate reagent for colorimetric measurements.

We claim:

1. A method of assaying a ligand in a sample which method comprises contacting a sample with components comprising
   (a) a specific binding partner to a ligand or
   (b) a specific binding partner to the ligand and at least one reagent selected from the group consisting of ligand analogues and specific binding partners,
   at least one of the said specific binding partner and said reagent being labelled with an electron-donor or electron-acceptor,
   and determining whether transfer of electrons between the said electron-donor or electron-acceptor label and a suitable charge-transfer partner resulting in charge-transfer complex formation is perturbed by at least one of (i) ligand complex formation and (ii) a controlled external influence which produces a perturbation of said transfer of electrons as a function of said ligand complex formation.

2. A method as claimed in claim 1, wherein the perturbation in the transfer of electrons is determined from an electrical measuring device connected to a solid surface capable of respectively accepting electrons from or donating electrons to the electron-donor or electron-acceptor label, the said surface constituting the charge-transfer partner for the label.

3. A method as claimed in claim 2, wherein the solid surface carries a layer of a chemical species capable of forming a charge-transfer complex with the label.

4. A method as claimed in claim 2 or claim 3 wherein the controlled external influence comprises displacement of the ligand complex formed by said contacting relative to the solid surface.

5. A method as claimed in claim 1, wherein the charge-transfer partner is a chemical species in solution capable of forming a coloured charge-transfer complex with the label and the perturbation in the transfer of electrons is determined from spectrophotometric measurements of the components and sample.

6. A method as claimed in claim 5, wherein the controlled external influence comprises displacement of the ligand complex formed by said contacting relative to unbound ligand present.

7. A method as claimed in claim 1 wherein the label is selected from the group consisting of electron-donors 1,3,5-trimethylbenzene, bis-$\pi$-benzene chromium and nitrobenzene and derivatives thereof and the electron-acceptors 1,3,5-trinitrobenzene, tetracyanoethylene, tetrathiofulvalene, tetranitrofluorenone and tetramethyl-phenanthroline and derivatives thereof.

8. A method as claimed in claim 1 wherein the ligand is an antigen or an antibody.

9. A method as claimed in claim 1, wherein the extent to which transfer of electrons is perturbed is determined.

10. A kit for use in a method of assay as claimed in claim 1, comprising, in separate containers, (i) at least one reagent selected from the group consisting of ligand analogues and specific binding partners labelled with an electron-donor or electron-acceptor capable of forming with a charge-transfer partner a charge-transfer complex, and (ii) a solid surface comprising a charge-transfer partner for said electron-donor or electron-acceptor capable of being connected to an electrical measuring device.

11. A kit for use in a method of assay as claimed in claim 1, comprising, in separate containers, (i) at least one reagent selected from the group consisting of ligand analogues and specific binding partners labelled with an electron-donor or electron-acceptor capable of forming with a charge-transfer partner a charge-transfer complex, and (ii) a chemical species capable of forming a colored charge-transfer complex with said electron-donor or electron-acceptor.

12. A kit as claimed in claim 11, which further comprises a spectrophotometric cell.

13. A ligand selected from the group consisting of antigens and antibodies labelled with a species selected from the group consisting of electron donors and electron acceptors capable of forming with a charge-transfer partner a charge-transfer complex.

14. A ligand as claimed in claim 13, in which said electron-donor is selected from the group consisting of 1,3,5-trimethylbenzene, bis-$\pi$-benzene chromium, nitrobenzene and electron donating derivatives thereof, and said electron-acceptor is selected from the group consisting of 1,3,5-trinitrobenzene, tetracyanoethylene, tetrathiofulvalene, tetranitrofluorenone, tetramethyl phenanthroline and electron accepting derivatives thereof.

* * * * *